(12) United States Patent
Greep

(10) Patent No.: US 11,033,253 B2
(45) Date of Patent: *Jun. 15, 2021

(54) ELECTROSURGICAL SCISSORS

(71) Applicant: Megadyne Medical Products, Inc., Draper, UT (US)

(72) Inventor: Darcy W. Greep, Herriman, UT (US)

(73) Assignee: Megadyne Medical Products, Inc., Draper, UT (US)

(*) Notice: Subject to any disclaimer, the term of this patent is extended or adjusted under 35 U.S.C. 154(b) by 112 days.

This patent is subject to a terminal disclaimer.

(21) Appl. No.: 16/146,559

(22) Filed: Sep. 28, 2018

(65) Prior Publication Data

US 2019/0029655 A1 Jan. 31, 2019

Related U.S. Application Data

(60) Continuation of application No. 15/290,740, filed on Oct. 11, 2016, now abandoned, which is a division of
(Continued)

(51) Int. Cl.
*A61B 18/14* (2006.01)
*A61B 10/02* (2006.01)
(Continued)

(52) U.S. Cl.
CPC ............ *A61B 10/02* (2013.01); *A61B 18/085* (2013.01); *A61B 18/1445* (2013.01);
(Continued)

(58) Field of Classification Search
CPC ....... A61B 18/12; A61B 18/14; A61B 18/085; A61B 18/1442; A61B 18/1445;
(Continued)

(56) References Cited

U.S. PATENT DOCUMENTS 4,534,347 A 8/1985 Taylor
4,674,498 A 6/1987 Stasz
(Continued)

OTHER PUBLICATIONS

Final Office Action for U.S. Appl. No. 14/749,142 dated Apr. 4, 2016.
(Continued)

*Primary Examiner* — Eugene T Wu
(74) *Attorney, Agent, or Firm* — Workman Nydegger

(57) ABSTRACT

Embodiments are directed to various monopolar and bipolar electrosurgical scissor instruments. A monopolar electrosurgical scissor instrument includes one scissor blade that has an electrically conductive tapered edge, where the tapered edge is insufficiently sharp to shear or otherwise mechanically cut tissue. The scissors also include another electrically insulated scissor blade movably mounted to the first scissor blade. The second scissor blade includes a flat contact surface that is aligned with the tapered edge of the first scissor blade. The scissors further include a scissor body that includes a conductor that transfers electrical energy from an energy source to the tapered edge of the first electrically conductive scissor blade to electrically cut interlaying tissue located between the first electrically conductive scissor blade and the second electrically insulated scissor blade.

17 Claims, 9 Drawing Sheets

Related U.S. Application Data application No. 14/749,142, filed on Jun. 24, 2015, now Pat. No. 9,463,060, which is a division of application No. 13/486,524, filed on Jun. 1, 2012, now Pat. No. 9,084,606.

(51) Int. Cl.
 *A61B 18/08* (2006.01)
 *A61B 18/00* (2006.01)

(52) U.S. Cl.
 CPC ............ *A61B 2018/0072* (2013.01); *A61B 2018/00589* (2013.01); *A61B 2018/00601* (2013.01); *A61B 2018/00875* (2013.01); *A61B 2018/146* (2013.01)

(58) Field of Classification Search
 CPC .... A61B 2018/00601; A61B 2018/142; A61B 2018/1452; A61B 2018/146
 See application file for complete search history.

(56) References Cited

U.S. PATENT DOCUMENTS

| | | |
|---|---|---|
| 4,785,807 A | 11/1988 | Blanch |
| 5,217,458 A | 6/1993 | Parins |
| 5,342,381 A | 8/1994 | Tidemand |
| 5,352,222 A | 10/1994 | Rydell |
| 5,380,320 A | 1/1995 | Morris |
| 5,478,350 A | 12/1995 | Kratsch et al. |
| 5,540,685 A | 7/1996 | Parins et al. |
| 5,603,711 A | 2/1997 | Parins et al. |
| 5,643,256 A | 7/1997 | Urueta |
| 5,693,050 A | 12/1997 | Speiser |
| 5,697,926 A | 12/1997 | Weaver |
| 5,702,387 A | 12/1997 | Arts et al. |
| 5,715,832 A | 2/1998 | Koblish et al. |
| 5,746,740 A | 5/1998 | Nicholas |
| 5,766,166 A | 6/1998 | Hooven |
| 5,776,128 A | 7/1998 | Eggers |
| 5,827,281 A | 10/1998 | Levin |
| 5,908,420 A | 6/1999 | Parins et al. |
| 6,024,744 A | 2/2000 | Kese et al. |
| 6,030,383 A | 2/2000 | Benderev |
| 6,039,735 A * | 3/2000 | Greep ............... A61B 18/1402 606/45 |
| 6,066,137 A | 5/2000 | Greep |
| 6,083,150 A | 7/2000 | Aznoian et al. |
| 6,102,909 A | 8/2000 | Chen et al. |
| 6,113,596 A | 9/2000 | Hooven et al. |
| 6,135,998 A | 10/2000 | Palanker |
| 6,152,923 A | 11/2000 | Ryan |
| 6,179,837 B1 | 1/2001 | Hooven |
| 6,206,877 B1 * | 3/2001 | Kese ............... A61B 18/1445 606/41 |
| 6,350,264 B1 | 2/2002 | Hooven |
| 6,358,249 B1 | 3/2002 | Chen et al. |
| 6,361,534 B1 | 3/2002 | Chen et al. |
| 6,364,879 B1 | 4/2002 | Chen et al. |
| 6,371,956 B1 | 4/2002 | Wilson et al. |
| 6,458,129 B2 | 10/2002 | Scarfi |
| 6,562,035 B1 | 5/2003 | Levin |
| 6,730,075 B2 | 5/2004 | Palanker et al. |
| 6,736,813 B2 | 5/2004 | Yamauchi et al. |
| 6,749,609 B1 | 6/2004 | Lunsford et al. |
| 6,780,178 B2 | 8/2004 | Palanker et al. |
| 6,932,810 B2 | 8/2005 | Ryan |
| 7,025,763 B2 | 4/2006 | Karasawa et al. |
| 7,033,356 B2 | 4/2006 | Latterell et al. |
| 7,052,496 B2 | 5/2006 | Yamauchi |
| 7,063,697 B2 | 6/2006 | Slater |
| 7,238,185 B2 | 7/2007 | Palanker et al. |
| 7,255,697 B2 | 8/2007 | Dycus et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,297,145 B2 | 11/2007 | Woloszko et al. |
| 7,316,683 B2 | 1/2008 | Kasahara et al. |
| 7,329,257 B2 | 2/2008 | Kanehira et al. |
| 7,344,536 B1 | 3/2008 | Lunsford et al. |
| 7,357,802 B2 | 4/2008 | Palanker et al. |
| 7,367,976 B2 | 5/2008 | Lawes et al. |
| 7,419,488 B2 | 9/2008 | Ciarrocca et al. |
| 7,419,490 B2 | 9/2008 | Falkenstein et al. |
| 7,458,972 B2 | 12/2008 | Keppel |
| 7,481,810 B2 | 1/2009 | Dumbauld et al. |
| 7,544,195 B2 | 6/2009 | Lunsford et al. |
| 7,594,916 B2 | 9/2009 | Weinberg |
| 7,645,278 B2 | 1/2010 | Ichihashi et al. |
| 7,717,912 B2 | 5/2010 | Woloszko et al. |
| 7,717,914 B2 | 5/2010 | Kimura |
| 7,736,361 B2 | 6/2010 | Palanker et al. |
| 7,789,879 B2 | 9/2010 | Palanker et al. |
| 7,887,535 B2 | 2/2011 | Lands et al. |
| 7,918,848 B2 | 4/2011 | Lau et al. |
| 7,931,649 B2 | 4/2011 | Couture et al. |
| 7,951,150 B2 | 5/2011 | Johnson et al. |
| 7,955,332 B2 | 6/2011 | Arts et al. |
| 7,972,333 B2 | 7/2011 | Nishimura |
| 8,123,746 B2 | 2/2012 | Suzuki |
| 9,084,606 B2 | 7/2015 | Greep |
| 9,463,060 B2 | 10/2016 | Greep |
| 2003/0109876 A1 | 6/2003 | Yamauchi |
| 2004/0068307 A1 | 4/2004 | Goble |
| 2005/0004569 A1 | 1/2005 | Witt et al. |
| 2006/0111711 A1 | 5/2006 | Goble |
| 2007/0203489 A1 * | 8/2007 | Suzuki ............... A61B 18/1445 606/51 |
| 2008/0015567 A1 | 1/2008 | Kimura |
| 2008/0195093 A1 * | 8/2008 | Couture ............ A61B 18/1445 606/45 |
| 2010/0030212 A1 | 2/2010 | Aramayo |
| 2011/0184410 A1 | 7/2011 | Greep et al. |
| 2017/0027550 A1 | 2/2017 | Greep |

OTHER PUBLICATIONS

Final Office Action for U.S. Appl. No. 131486,524 dated Dec. 1, 2014.

Non-Final Office Action for U.S. Appl. No. 13/486,524 dated Aug. 19, 2014.

Non-Final Office Action for U.S. Appl. No. 14/749,142 dated Jan. 6, 2016.

Notice of Allowance for U.S Appl. No. 13/486,524 dated Mar. 17, 2015.

* cited by examiner

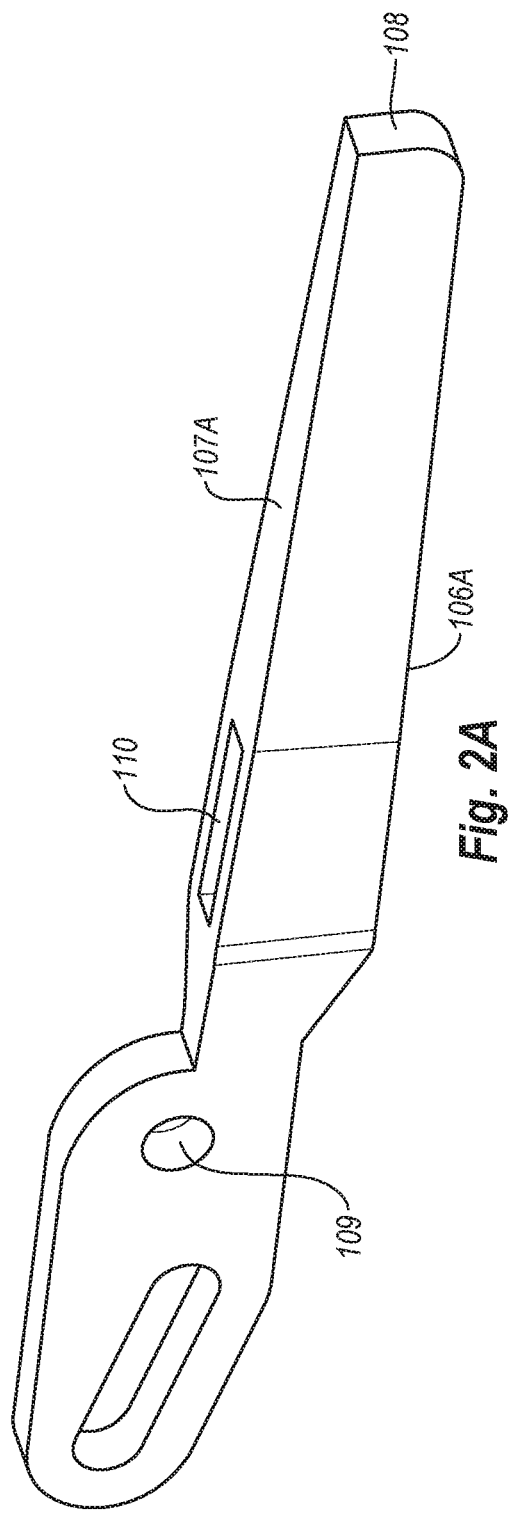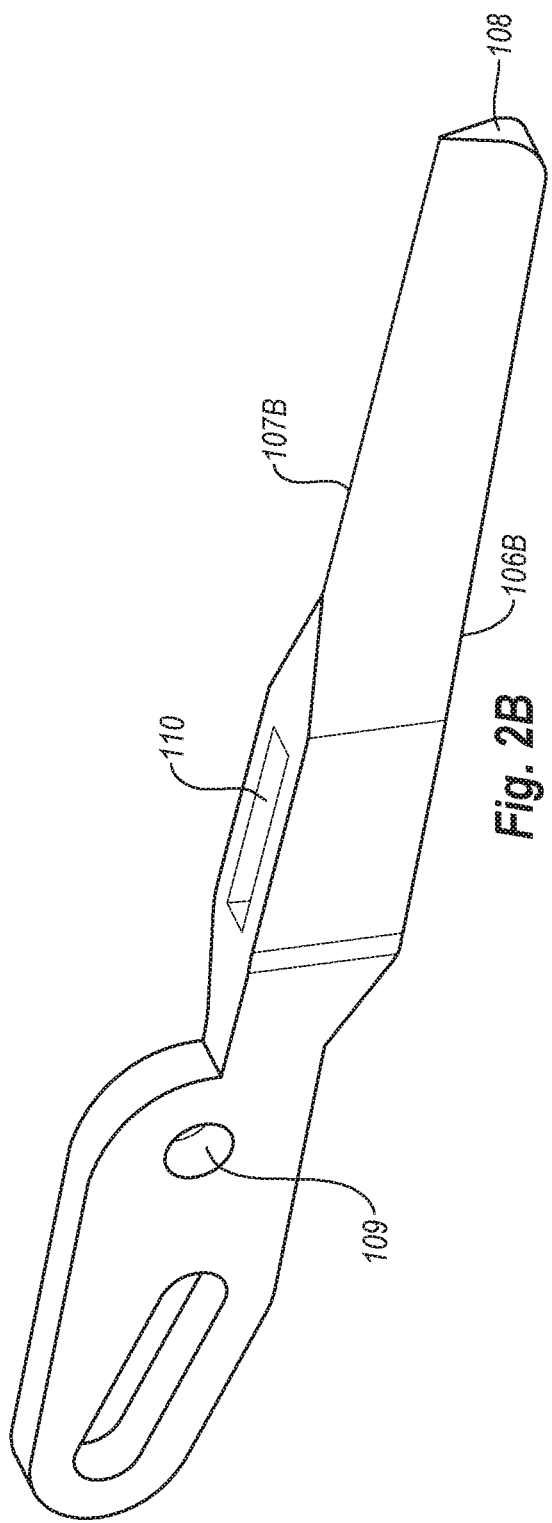

ELECTROSURGICAL SCISSORS

CROSS-REFERENCE TO RELATED APPLICATIONS

This application is a continuation of U.S. patent application Ser. No. 15/290,740, filed Oct. 11, 2016, and entitled "ELECTROSURGICAL BIOPSY INSTRUMENT," which is a divisional of U.S. patent application Ser. No. 14/749,142, filed Jun. 24, 2015, and entitled "ELECTROSURGICAL SCISSORS," which is a divisional of U.S. patent application Ser. No. 13/486,524, filed Jun. 1, 2012, and entitled "ELECTROSURGICAL SCISSORS," the disclosures of each of which are incorporated herein by this reference in their entireties.

BACKGROUND

Historically, tissue has been cut with scissors of various designs by a mechanical shearing action as sharpened blades move past each other on closing. The mechanical limitations of typical scissor designs and the variation in tissue types result in the following problems and complications: tissue squeezing out of the scissor on compression ("popping out"); incomplete cuts; cut edges that are uneven (caused by dull scissors or changes in tissue type); the inability to see/determine exactly what is being cut; separation and jamming of scissor blades without cutting tissue when fibrous, fatty, or tough tissue gets caught between blades; and dulling of the scissors due to limitations of materials and mechanisms. Additionally, the sharp blades of traditional scissors may inadvertently nick or damage other tissues or structures, such as nerves, blood vessels, tendons, sutures, implanted electrical leads (pacemaker, defibrillator, neural stim, etc.) and surgical personnel. Furthermore, general scissor designs do not provide a mechanism to stop bleeding once tissue has been cut.

With the advent of electrosurgery, both monopolar and bipolar scissor designs have been produced to allow for application of electrical energy to stop bleeding after tissue has been cut with the scissors. These designs have attempted to combine both the mechanical shearing action of a regular scissor and the application functionality of electrosurgical energy in both cut and coagulation modes. However, attempts to concentrate electrical energy in a focused manner to enhance the cutting effect have been sparse. Indeed, most efforts have been with bipolar instruments which typically attempt to achieve a small activation zone effect through optimal electrode distances and placement.

BRIEF SUMMARY

Embodiments described herein are directed to various monopolar and bipolar electrosurgical scissor instruments. In one embodiment, a monopolar electrosurgical scissor instrument includes one scissor blade that has an electrically conductive tapered edge that is insufficiently sharp to shear or otherwise mechanically cut tissue. The scissors also include another electrically insulated scissor blade movably mounted to the first scissor blade. The second scissor blade includes a contact surface that is aligned with the tapered edge of the first scissor blade. The contact surface of the second scissor blade may be a substantially flat edge or a tapered edge. The scissors further include a scissor body that is or has a conductor that selectively transfers electrical energy from an energy source to the tapered edge of the first electrically conductive scissor blade to electrically cut interlaying tissue located between the first electrically conductive scissor blade and the second electrically insulated scissor blade. The scissor body may also include a switch for selectively activating the energy source that supplies electrical energy to the scissor. Conversely, the switch may be located separately from the scissor such as a footswitch activation mechanism.

In another embodiment, an alternative monopolar electrosurgical scissor instrument is provided. The scissors include a scissor blade that has an electrically conductive tapered edge that is insufficiently sharp to shear or otherwise mechanically cut tissue. The scissors also include a second electrically conductive scissor blade movably mounted to the first scissor blade. The second scissor blade includes a contact surface that is aligned with the tapered edge of the first scissor blade. The contact surface of the second scissor blade may be a substantially flat edge or a tapered edge. The first scissor blade and the second scissor blade are electrically connected to one another. The scissors further include a scissor body that is or has a conductor that transfers a monopolar output signal from an energy source to the tapered edge of the first electrically conductive scissor blade to electrically cut interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

In another embodiment, an alternative monopolar electrosurgical scissor instrument is provided. The scissors include a scissor blade that has an electrically conductive tapered edge that is insufficiently sharp to shear or otherwise mechanically cut tissue. The scissors also include a second electrically conductive scissor blade movably mounted to the first scissor blade. The second scissor blade includes a contact surface that is aligned with the tapered edge of the first scissor blade. The contact surface of the second scissor blade may be a substantially flat edge or a tapered edge. The first scissor blade and the second scissor blade are electrically insulated from one another. A minimum clearance space is provided between the first and second blades to prevent the first and second blades from touching. The scissors further include a scissor body that is or has a conductor that transfers a monopolar output signal from an energy source to the tapered edge of the first electrically conductive scissor blade to electrically cut interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

In another embodiment, an alternative monopolar electrosurgical scissor instrument is provided. The scissors include a scissor blade that has an electrically conductive tapered edge that is insufficiently sharp to shear or otherwise mechanically cut tissue. The scissors also include a second electrically conductive scissor blade movably mounted to the first scissor blade. The second scissor blade includes a contact surface that is aligned with the tapered edge of the first scissor blade. The contact surface of the second scissor blade may be a substantially flat edge or a tapered edge. The first scissor blade and the second scissor blade are electrically insulated from one another. A minimum clearance space is provided between the first and second blades to prevent the first and second blades from touching. The scissors further include a scissor body that is or has two conductors. One conductor selectively transfers a monopolar output signal from an energy source to the tapered edge of the first electrically conductive scissor blade. The second conductor acts as a return lead for the monopolar signal and electrically connects the second electrically conductive scissor blade to the return input of the ESU. When activated this arrangement serves to electrically cut interlaying tissue located between the first electrically conductive scissor blade and the second electrically conductive scissor blade. The scissor body may also include a switch for selectively activating the energy source that supplies electrical energy to the first scissor blade. Conversely, the switch may be located separately from the scissor such as a footswitch activation mechanism.

In still another embodiment, a bipolar electrosurgical scissor instrument is provided. The scissors include a scissor blade that has an electrically conductive tapered edge that is insufficiently sharp to shear or otherwise mechanically cut tissue. The scissors also include a second electrically conductive scissor blade being movably mounted to the first electrically conductive scissor blade. The second scissor blade has a contact surface that is aligned with the tapered edge of the first scissor blade. The contact surface of the second scissor blade may be a substantially flat edge or a tapered edge. The scissors also include a scissor body that is or has conductors that transfer electrical energy from an energy source to the tapered edge of the first electrically conductive first scissor blade in a first polarity and transfers electrical energy to the substantially flat contact surface of the second scissor blade in a second polarity that is opposite from the first polarity. The transferred energy electrically cuts interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments of the invention may be realized and obtained by means of the instruments and combinations particularly pointed out in the appended claims. Features of the embodiments of the present invention will become more fully apparent from the following description and appended claims, or may be learned by the practice of the invention as set forth hereinafter.

BRIEF DESCRIPTION OF THE DRAWINGS

To further clarify the above and other advantages and features of embodiments of the present invention, a more particular description of embodiments of the present invention will be rendered by reference to the appended drawings. It is appreciated that these drawings depict only typical embodiments of the invention and are therefore not to be considered limiting of its scope. The embodiments of the invention will be described and explained with additional specificity and detail through the use of the accompanying drawings in which:

FIG. 2A illustrates an isometric view of an electrosurgical scissor blade with a substantially flat top surface.

FIG. 2B illustrates an isometric view of an electrosurgical scissor blade with a tapered top surface.

DETAILED DESCRIPTION

Figure 1:
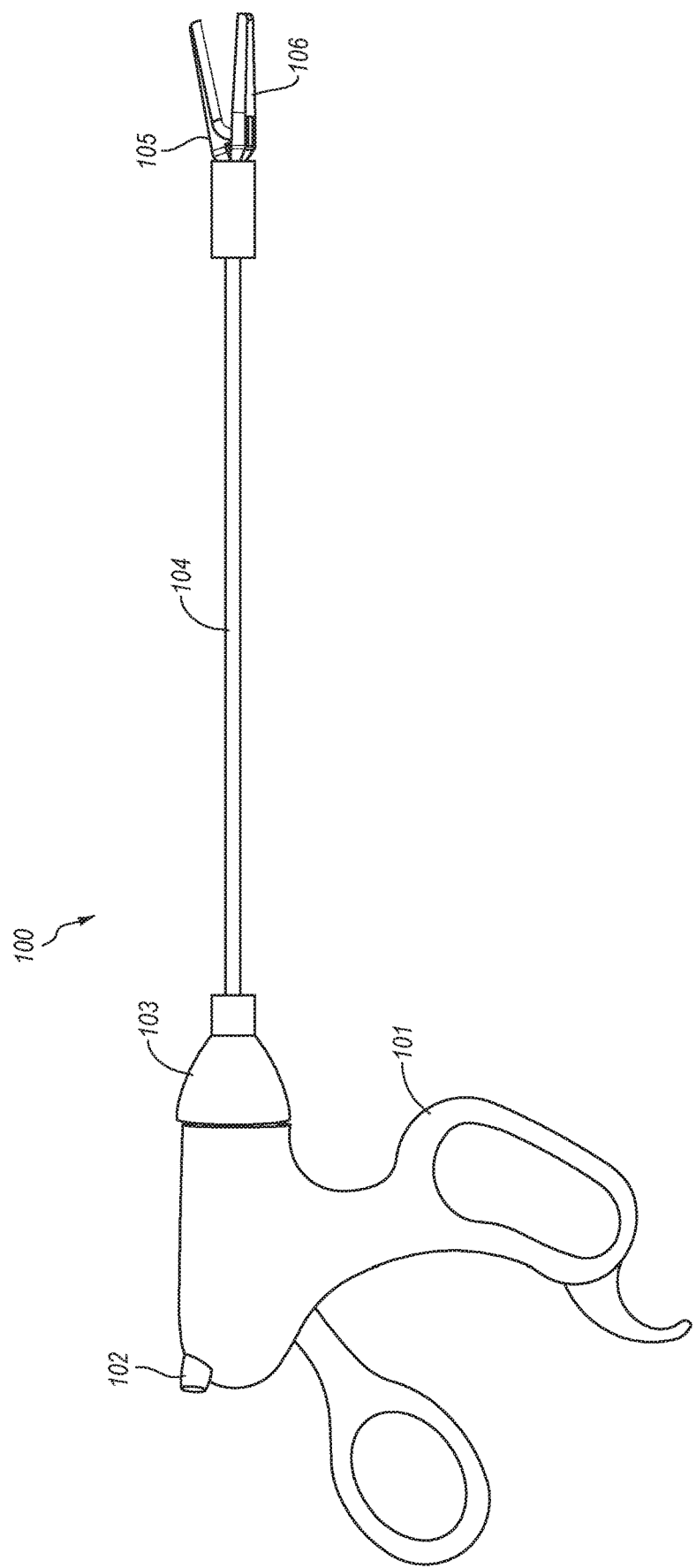
FIG. 1 illustrates a side view of a laparoscopic electrosurgical device according to one embodiment.

Embodiments described herein are directed to various monopolar and bipolar electrosurgical scissor instruments. In one embodiment, a monopolar electrosurgical scissor instrument includes one scissor blade that has an electrically conductive tapered edge that is insufficiently sharp to shear or otherwise mechanically cut through tissue. The scissors also include another electrically insulated scissor blade movably mounted to the first scissor blade. The second scissor blade includes a contact surface that is aligned with the tapered edge of the first scissor blade. The contact surface of the second scissor blade may be a substantially flat edge or a tapered edge. The scissors further include a scissor body that is or has a conductor that transfers electrical energy from an energy source to the tapered edge of the first electrically conductive scissor blade to electrically cut interlaying tissue located between the first electrically conductive scissor blade and the second electrically insulated scissor blade. The scissor body may also include a switch for selectively activating the energy source that supplies electrical energy to the scissor. Conversely, the switch may be located separately from the scissor such as a footswitch activation mechanism.

In another embodiment, an alternative monopolar electrosurgical scissor instrument is provided. The scissors include a scissor blade that has an electrically conductive tapered edge that is insufficiently sharp to shear or otherwise mechanically cut through tissue. The scissors also include a second electrically conductive scissor blade movably mounted to the first scissor blade. The second scissor blade includes a contact surface that is aligned with the tapered edge of the first scissor blade. The contact surface of the second scissor blade may be a substantially flat edge or a tapered edge. The first scissor blade and the second scissor blade are electrically insulated from one another. A minimum clearance space is provided between the first and second blades to prevent the first and second blades from touching. The scissors further include a scissor body that is or has a conductor that transfers a monopolar output signal from an energy source to the tapered edge of the first electrically conductive scissor blade to electrically cut interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

In another embodiment, an alternative monopolar electrosurgical scissor instrument is provided. The scissors include a scissor blade that has an electrically conductive tapered edge that is insufficiently sharp to shear or otherwise mechanically cut through tissue. The scissors also include a second electrically conductive scissor blade movably mounted to the first scissor blade. The second scissor blade includes a contact surface that is aligned with the tapered edge of the first scissor blade. The contact surface of the second scissor blade may be a substantially flat edge or a tapered edge. The first scissor blade and the second scissor blade are electrically insulated from one another. A minimum clearance space is provided between the first and second blades to prevent the first and second blades from touching. The scissors further include a scissor body that is or has two conductors. One conductor transfers a monopolar output signal from an energy source to the tapered edge of the first electrically conductive scissor blade. The second conductor acts as a return lead for the monopolar signal and electrically connects the second electrically conductive scissor blade to the return input of the ESU. The first conductor selectively transfers a monopolar output signal from an energy source to the tapered edge of the first electrically conductive scissor blade to electrically cut interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

In still another embodiment, a bipolar electrosurgical scissor instrument is provided. The scissors include a scissor blade that has an electrically conductive tapered edge that is insufficiently sharp to shear or otherwise mechanically cut tissue. The scissors also include a second electrically conductive scissor blade being movably mounted to the first electrically conductive scissor blade. The second scissor blade has a contact surface that is aligned with the tapered edge of the first scissor blade. The contact surface of the second scissor blade may be a substantially flat edge or a tapered edge. The scissors also include a scissor body that is or has a conductor that transfers electrical energy from an energy source to the tapered edge of the first electrically conductive first scissor blade in a first polarity and transfers electrical energy to the substantially flat contact surface of the second scissor blade in a second polarity that is opposite from the first polarity. The transferred energy electrically cuts interlaying tissue located between the first electrically conductive scissor blade and the second electrically conductive scissor blade. The scissor body may also include a switch for selectively activating the energy source that supplies electrical energy to the scissor. Conversely, the switch may be located separately from the scissor such as a footswitch activation mechanism.

Each of the above embodiments will be described with reference to FIGS. 1-5 below. FIG. 1 illustrates a laparoscopic electrosurgical device 100 that may be used in various laparoscopic or other minimally invasive surgeries. The laparoscopic electrosurgical device 100 includes various parts that function together to sever tissue, as directed by the operator (typically, a surgeon). For instance, the device 100 includes a handle 101. The handle may be designed such that squeezing the lever of the handle toward the other part of the handle activates one or both of the electrosurgical scissor blades (105 & 106). This activation may lower the top scissor blade 105 onto the bottom scissor blade 106. Additionally or alternatively, squeezing the lever of the handle may initiate the flow of electrical current to one or both of the electrosurgical scissor blades (105 & 106). In other cases, the handle 101 (or another part of the device 100) may include a separate switch or button (not shown) that initiates the flow of electrical energy to one or both of the electrosurgical blades. In still other cases, a switch mechanism such as a foot switch may be used to initiate the flow of electrical energy to one or both of the electrosurgical blades.

The handle (or any other part of the laparoscopic electrosurgical device 100) may include an input 102 for electrical energy. This electrical energy may be used to electrically cut any tissue that is between the top blade 105 and the bottom blade 106. The electrical energy is received from a local or remote power source, such as an electrosurgical generator (ESU). The power source may be designed to provide a specified amount of electrical energy or current with a specified waveform to one or both of the electrosurgical scissor blades (105 and/or 106). The electrical energy is carried over a wire or other electrical conductor through an elongated shaft 104 to the scissor blade(s). In some embodiments, the laparoscopic electrosurgical device 100 may include cap 103 that separates the handle 101 and the elongated shaft 104. In some embodiments, the shaft 104 and scissor blades 105/106 of the laparoscopic electrosurgical device 100 may be inserted into a patient's body up to the cap 103. In this manner, the scissor blades can be used to cut tissue within the patient's body, without having to make a large incision in the patient's body. As laparoscopic surgical devices are generally known in the art, the discussion below will focus on the electrosurgical blades 105 and 106.

The electrosurgical scissor blades 105 and 106 may be referred to herein as "energy concentrating scissors", "energy concentrating scissor blades", or simply "electrosurgical blades". Energy concentrating scissors use high density (highly focused) electrical energy to cut through tissue after it has been captured in the closed scissors. Because the electrosurgical blades are not sufficiently sharp to shear or otherwise mechanically cut tissue, tissue may be grasped by the scissors without cutting the tissue. The electrosurgical blades will only cut the tissue when electrical current is applied. As such, a doctor or other user may grasp the tissue between the scissor blades 105 and 106 and, after confirming the desired location, positioning, or tissue, may initiate the flow of electricity to one or both scissor blades 105/106. The electrical energy is concentrated along the tapered edge 113 (FIG. 3) of the scissor blade 105 and the blade cuts through the intervening tissue.

The energy concentrating scissors of the present disclosure present various advantages. For instance, tissue can be firmly grasped or captured in the closed electrosurgical scissors without cutting the tissue. When the tissue is firmly grasped by the closed scissors, the tissue may be retracted or pulled away from other bodily structures for viewing prior to electrically cutting the tissue (i.e. activation of electrical energy to one or both of the scissor blades). This allows the doctor or other user to identify tissues and structures that will be cut prior to actually making the cut. The doctor can even pull tissues away from sensitive structures such as nerves, blood vessels, ducts, tendons, etc. to ensure accidental damage does not occur.

The fact that the disclosed electrosurgical scissors do not cut by mechanical shearing provides additional benefits. For instance, since a cut is made using electrical energy, there are less compression forces applied to the intervening tissue as a cut is made. As a result, the intervening tissue squeezes and "pops out" less during a cutting procedure. Additionally, the electrosurgical scissors do not become dull like mechanical shearing scissors do after repeated use. As such, tissue cuts do not become uneven due to dullness. Moreover, a change in tissue type does not affect the direction of the cut, which aids in preventing uneven edges.

Furthermore, the electrosurgical scissor blades are not mechanically sharp enough to cut tissue, structures, etc. Rather, the scissor blades are designed to only cut tissue that is in contact with a return signal path (e.g. the return path from blade 105 to blade 106). The surgeon or other user cannot accidentally cut him- or herself or other surgical personnel, or other surrounding nonconductive items such as sutures or gloves. Moreover, since scissor action of the electrosurgical scissors does not include blades moving past each other (e.g., in a mechanical shearing action), tissue does not get caught between blades and cause separation and/or jamming of the scissors.

The presently disclosed scissor blades may be coated with an insulating material. This coating or insulation may cover the entire blade, or may coat the entire blade with the exception of the concentrating edge 113 of the electrosurgical scissors. The insulating material may include one or more layers of various different materials. Examples of such materials include Polytetrafluoroethylene (PTFE), silicone, other high temperature polymers, glass, ceramic, other silica based insulating materials, etc. The coating may acts as both a non-stick coating and a dielectric layer to help focus energy along the edge of the scissor blade.

Focused electrical energy produces minimal to no thermal necrosis (spread) during activation and cutting. The cut is clean and thermal damage to adjacent tissue is minimized. The electrosurgical scissors may use a relatively low amount of power to generate the cut effect (e.g. in the range of 20-50 Watts). As such, small structures and thin membranes can be safely cut without damage to neighboring tissue outside the incision line. In some embodiments, coagulation energy may also be delivered with the active scissor blade to stop bleeding at or near the cut. Vessels may even be grasped and sealed with the application of coagulation waveform energy.

The energy concentrating scissors 100 may be implemented in substantially any scissor style design, including those which currently use a mechanical shearing or cutting action to cut tissue. These styles may include, but are not limited to, hand-held scissors such as: straight tipped, curved tip, Iris scissors, Mayo scissors, Metzenbaum scissors, Dura scissors, Braun-Stadler Episiotomy scissors, micro scissors, endoscopic scissors and others. It is also applicable to laparoscopic scissors and other minimally invasive cutting instruments.

In some embodiments, the electrosurgical scissors are designed to have an electric energy concentrating edge 113. This tapered edge may have a width of about 0.2 mm or less. This allows for a sharpened edge which is not sharp enough to mechanically cut by itself, but which focuses and concentrates the electrical energy in a way that easily cuts through tissue. A coating such as PTFE or other types of fluoropolymers, silicone, other high temperature organic polymers, glass, ceramic, organosilicones and other high temperature combination polymers, diamond, as well as any other high temperature resistant, electrically insulative materials may be used to coat or cover the scissor tip(s) 108, as well as the whole scissor body or portions of the scissor body 105. The edge of the cutting surface 113 may be fully coated, left uncoated, or cleaned of coating, depending on the insulation value and other coating characteristics of the chosen material in order to focus the electrical energy. In this way, mechanical shearing is eliminated as the cutting mechanism, and tissue may be grasped prior to cutting for evaluation and exclusion of tissues or structures that need to be protected.

Figure 3:
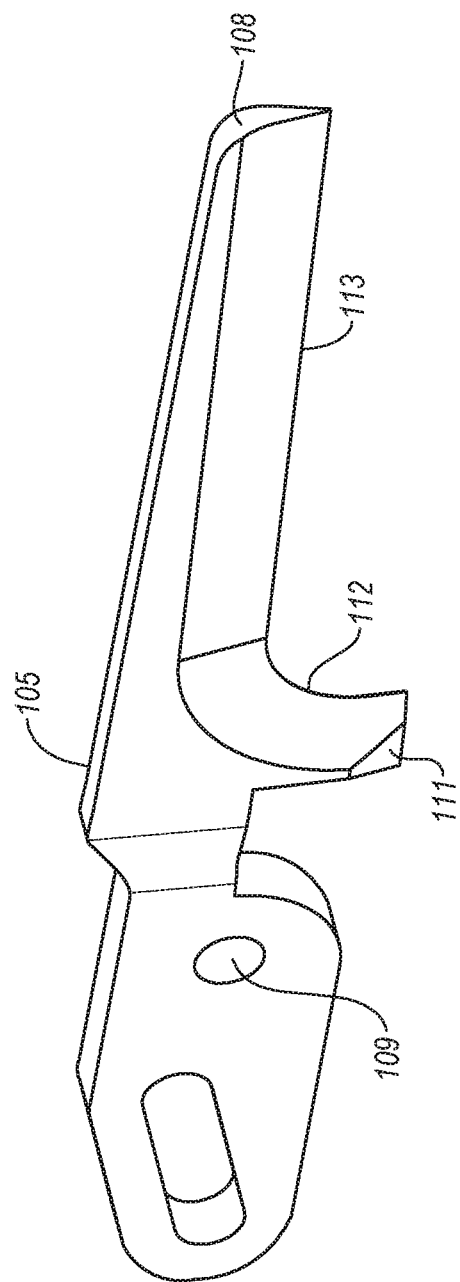
FIG. 3 illustrates an isometric view of an electrosurgical scissor blade with a tapered bottom surface.
Figure 4A:
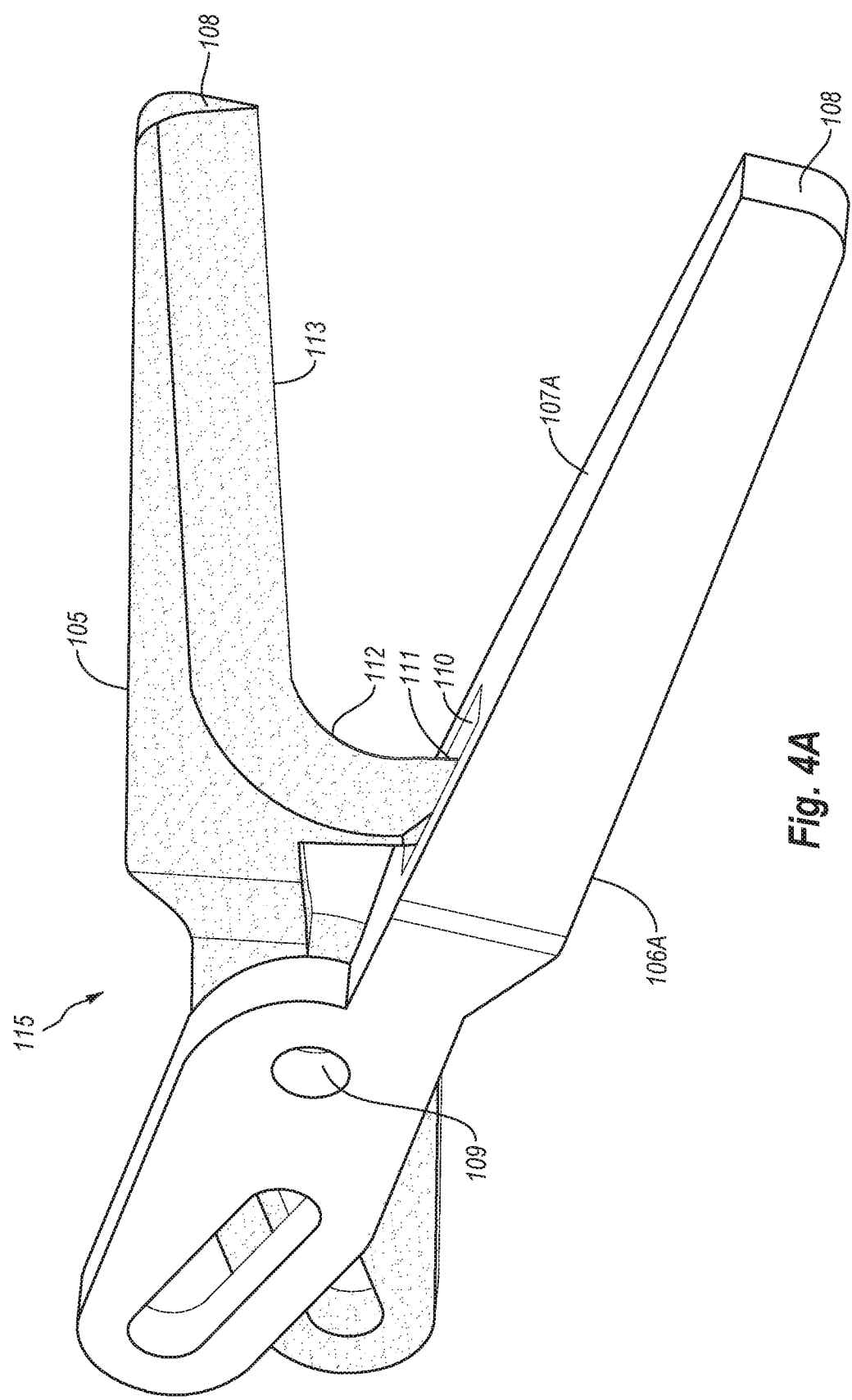
FIG. 4A illustrates an isometric view of two electrosurgical scissor blades in which the top blade is powered with electrical energy.

FIG. 4A incorporates the elements of FIGS. 2A and 3. As shown in FIG. 4A, a monopolar electrosurgical scissor instrument 115 may be provided. The electrosurgical scissors include a top scissor blade 105 that has an electrically conductive tapered edge 113. As shown by itself in FIG. 3, the top blade 105 has a tapered edge 113 that is insufficiently sharp to mechanically shear or otherwise cut tissue. As explained above, the edge 113 may be tapered to a width of about 0.2 mm or less.

The tapered edge 113 of the top scissor blade 105 may also include a dropdown rounded corner 112. The dropdown rounded corner 112 allows continuous electrosurgical tissue cutting. Accordingly, if electrical energy is flowing to the top scissor blade 105, the dropdown rounded corner may slide through tissue, electrically cutting the tissue in a continuous motion, without requiring the scissor blades to open and close on the tissue. Like edge 113, however, the dropdown rounded corner 112 is not sharp enough to mechanically shear or otherwise cut tissue. Slide cuts are only performed when electrical energy is flowing to the scissor blade 105.

Figure 5:
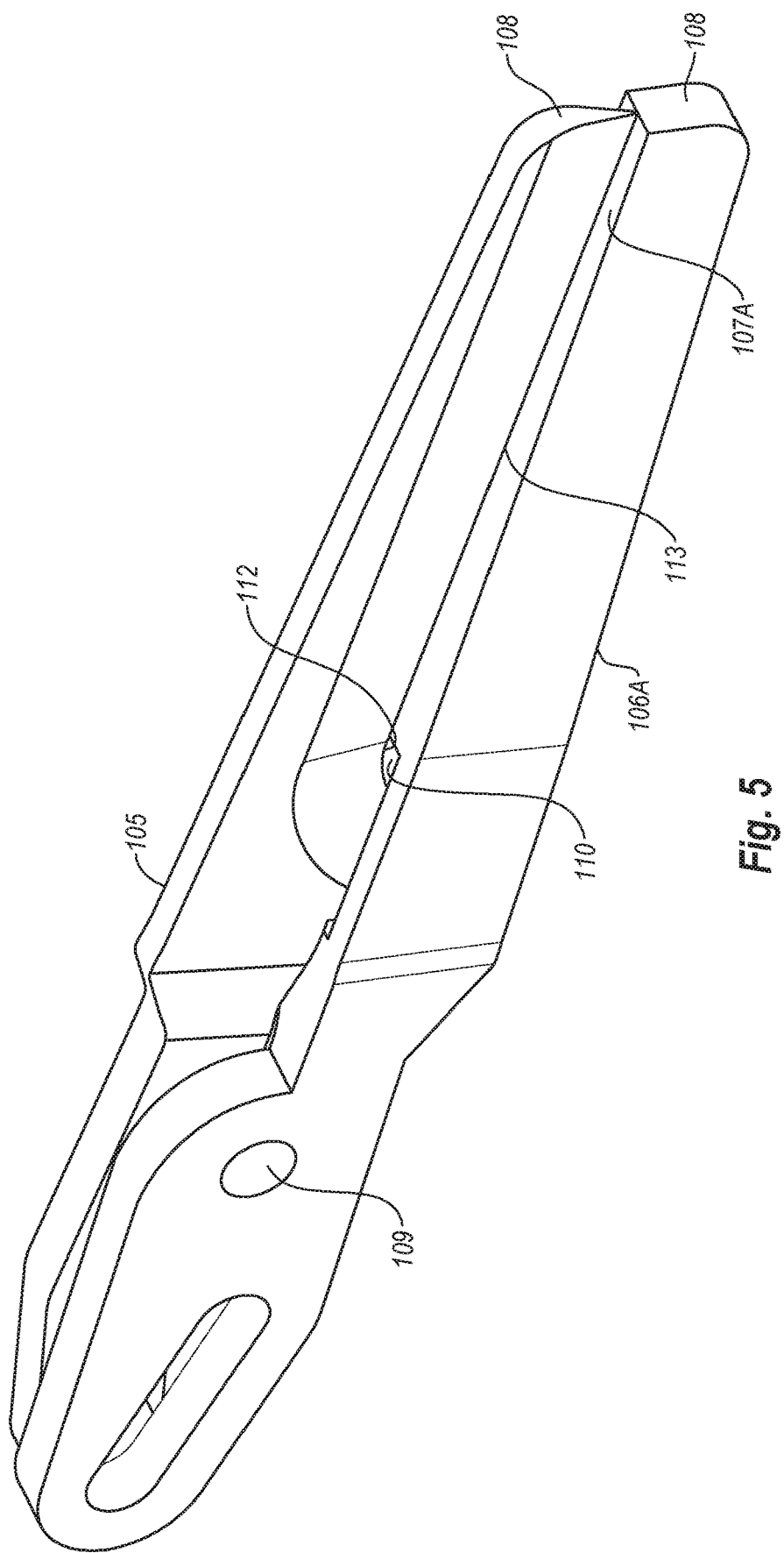
FIG. 5 illustrates an isometric view of two electrosurgical scissor blades in a closed position.

The monopolar scissors 115 also include an electrically insulated bottom scissor blade 106A that is positioned below the top blade 105 and is movably mounted to the top scissor blade. As shown in FIG. 2A, the bottom scissor blade 106A includes a substantially flat contact surface 107A that is aligned with the tapered edge 113 of the top scissor blade 105. The bottom scissor blade 106A, like the top blade 105, includes a mounting hole 109 through which a mounting pin or other fastening mechanism may be used to fasten the two scissor blades together. The scissor blades may separate (as shown in FIG. 4A) to allow the insertion of tissue between the blades. The blades may then be closed as shown in FIG. 5. The bottom scissor blade 106A includes a cavity 110 through which the interlocking portion 111 and/or a portion of the dropdown rounded corner 112 of the top blade 105 is allowed to pass. The cavity and interlocking portion may align the scissor blades to ensure that the blades do not bend or twist in response to pressure applied to the tissue. The cavity 110 may also simply allow at least of portion of the dropdown rounded corner 112 to be inserted therein as the scissors are closed.

In some cases, as shown in FIG. 2B, the bottom scissor blade 106B may have a tapered edge 107B. In such cases, both the top blade 105 and the bottom blade 106B include tapered edges (113 and 107B, respectively). As with the top scissor blade's tapered edge 113, the bottom blade's tapered edge 107B is insufficiently sharp to shear or otherwise mechanically cut tissue. The cutting occurs only when electrical energy is applied. The bottom scissor blade, whether tapered (106B) or flat (106A) may be electrically insulated, or may be electrically conductive. Likewise, whether tapered (106B) or flat (106A), the bottom scissor blade may include a cavity 110 for receiving the dropdown rounded corner 112 of the top scissor blade 105.

The bottom scissor blade 106 may be toothed to clamp tissue between the top scissor blade 105 and the bottom scissor blade. The teeth may be substantially any shape or size, and may be arranged in any of a variety of different patterns. Additionally or alternatively, the bottom scissor blade may be U-shaped to clamp tissue between the top and bottom blades. The outside edges of the top and bottom scissor blades may be blunted to allow blunt dissections. Thus, the blunt tips 108 may be inserted into a body cavity, and the scissor blades may be used to separate tissues in the cavity without mechanically or electrically cutting those tissues.

The electrical energy used to perform the cutting in the monopolar electrosurgical device 115 may include a pulse waveform that varies the amount of current delivered to the scissor blade(s) based on a determined impedance level of the tissue. Thus, current may be delivered to the electrically conductive top scissor blade 105 to perform a cut. The current may vary depending on a measured impedance level of the tissue being cut. This impedance level may increase or decrease based on the amount or type of tissue that is currently between the top and bottom blades (105 and 106). If there is a greater amount of tissue, or if there is a denser type of tissue, more current may be sent to the blade(s). Conversely, if there is a lesser amount of tissue, or if there is a less dense type of tissue currently between the blades, less current may be sent to the blade(s) to cut the tissue. A coagulation signal may also be sent through the top electrically conductive scissor blade 105, the bottom electrically conductive scissor blade 106, or the top and bottom electrically conductive scissor blades (105 and 106) to coagulate surrounding tissues. The coagulation signal may thus be delivered through the active scissor tip(s) to help stop bleeding of cut tissues and vessels. This design may also be employed as a cutting blade for vessel sealers to cut tissue that has been, or is about to be sealed. This may, at least in some embodiments, replace mechanical cutters often used in commercial vessel sealing products.

The monopolar electrosurgical scissors 115 further include a scissor body (as shown in the laparoscopic electrosurgical device 100 of FIG. 1) that includes a switch or lever 101 that selectively transfers electrical energy from an energy source to the tapered edge 113 of the electrically conductive top scissor blade 105. When activated, electrical energy is transferred to the top scissor blade 105 which then cuts interlaying tissue located between the top electrically conductive scissor blade 105 and the bottom electrically insulated scissor blade 106A.

Figure 4B:
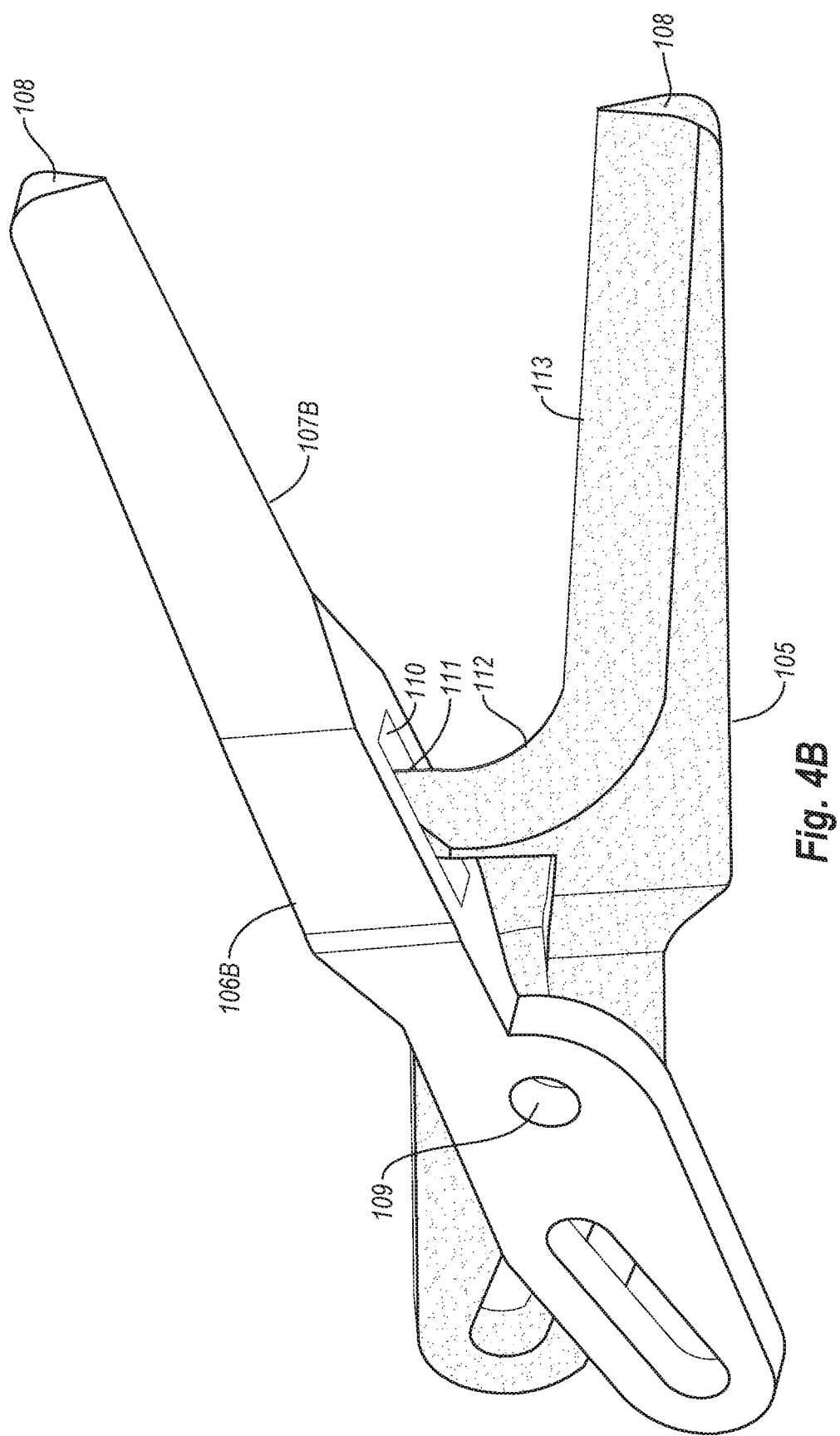
FIG. 4B illustrates an isometric view of two electrosurgical scissor blades in which the bottom blade is powered with electrical energy.
Figure 4C:
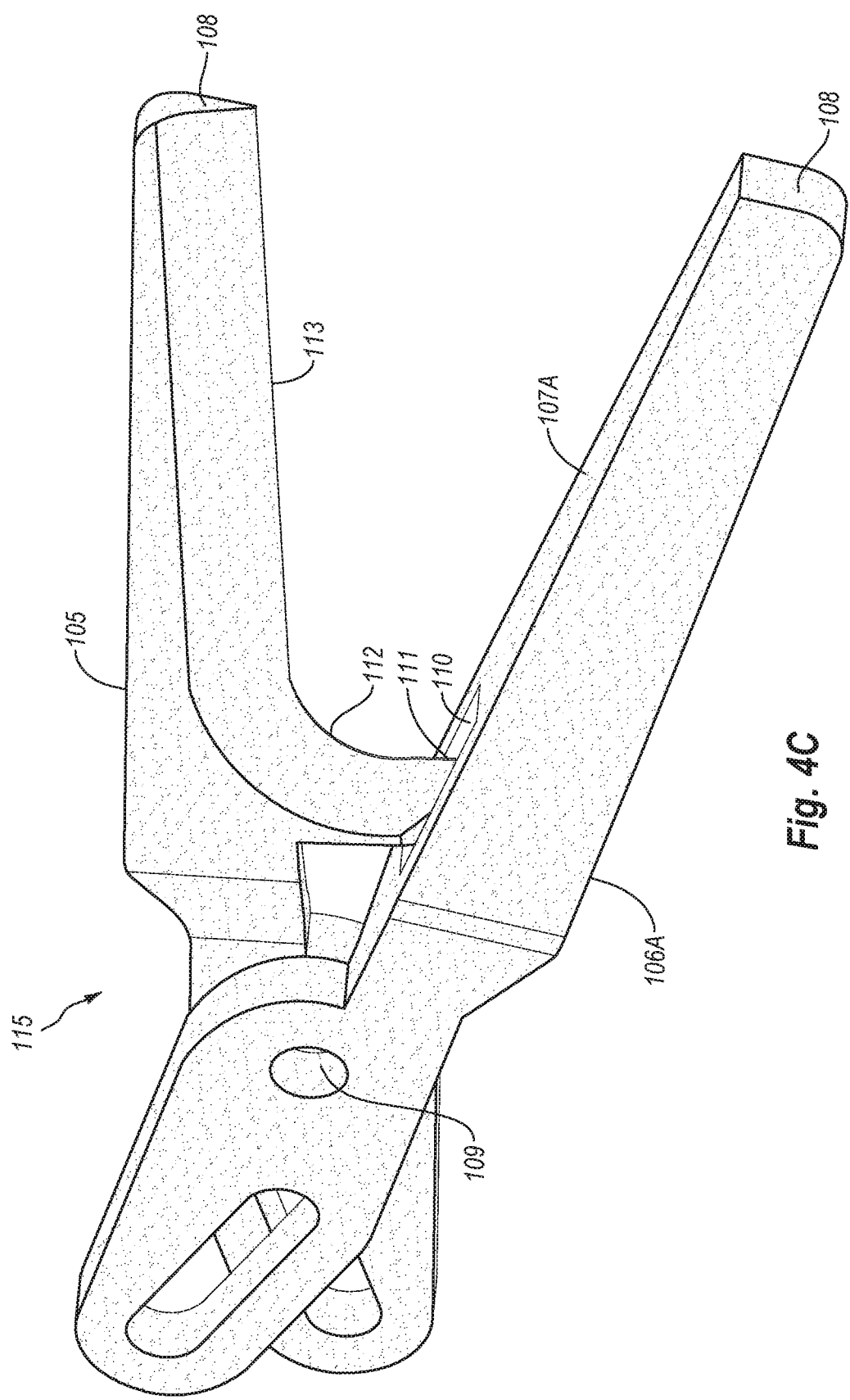
FIG. 4C illustrates an isometric view of two electrosurgical scissor blades in which both the top and bottom blades are powered with electrical energy, and where the bottom blade has a substantially flat top surface.

In another embodiment, shown in FIG. 4C, an alternative monopolar electrosurgical scissor instrument is provided. The electrosurgical scissors include a top scissor blade 105 having an electrically conductive tapered edge 113. The tapered edge 113 is insufficiently sharp to shear or otherwise mechanically cut tissue. The scissors also include a bottom electrically conductive scissor blade 106 movably mounted to the first scissor blade 105. The bottom scissor blade includes a substantially flat contact surface 107A that is aligned with the tapered edge 113 of the top scissor blade. Thus, when the top scissor blade is lowered to the flat contact surface 107A, the two blades meet, as shown in FIG. 5. In some cases, the bottom scissor blade 106B may include a tapered edge 107B (as shown in FIG. 2B).

In this embodiment, the top scissor blade 105 and the bottom scissor blade 106 are electrically insulated from one another, and a minimum clearance space is provided between the top and bottom blades to prevent the top and bottom blades from touching when the scissor is closed. In some cases, the electrosurgical scissors may be designed to allow electrical current to be returned via an electrically conductive bottom blade. Thus, various embodiments are possible.

Figure 4D:
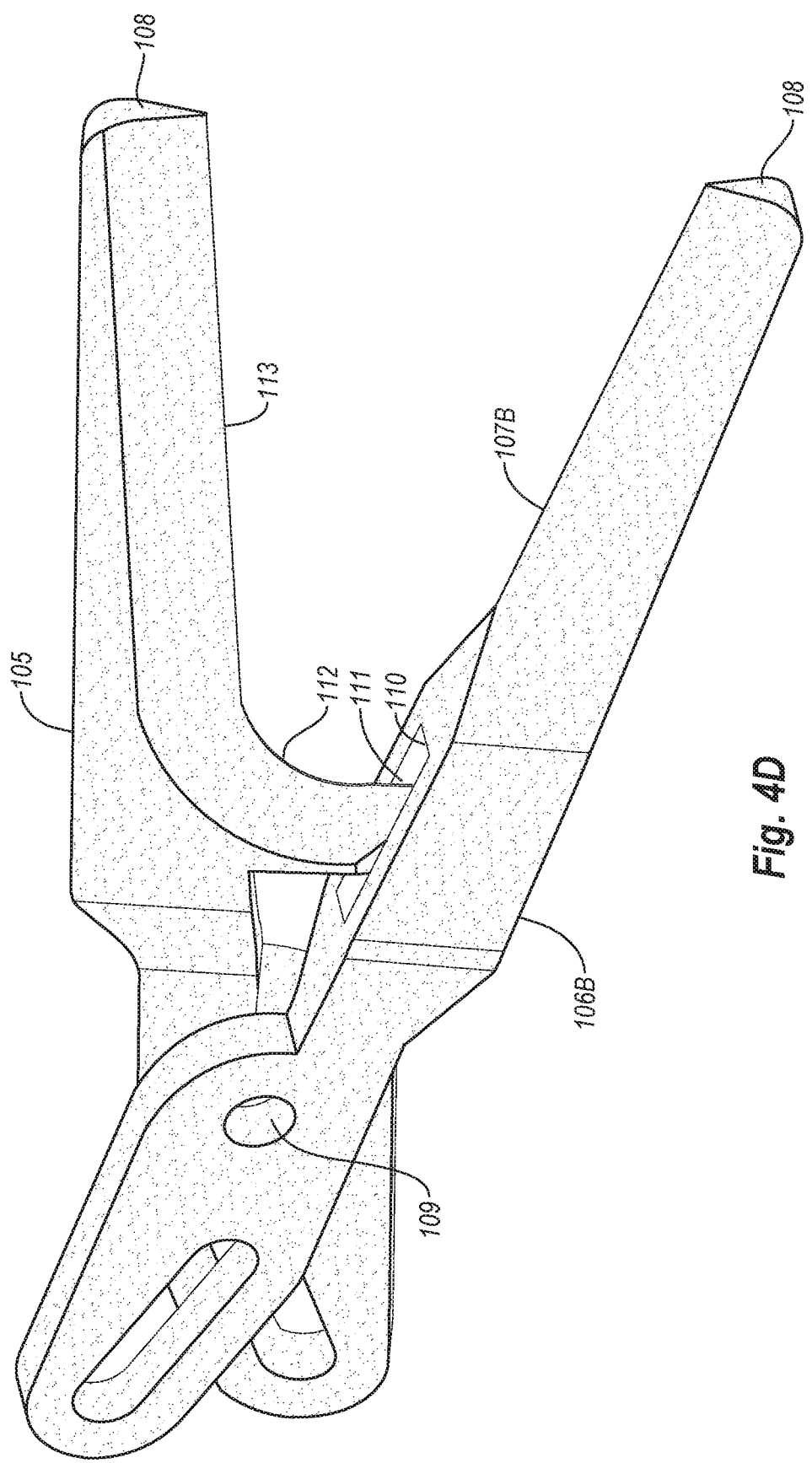
FIG. 4D illustrates an isometric view of two electrosurgical scissor blades in which both the top and bottom blades are powered with electrical energy, and where the bottom blade has a tapered top surface.

As shown in FIG. 4A, shading on the top blade 105 indicates that the top blade is conductive and can allow electrical current to flow through it. FIG. 4B illustrates an embodiment where the top blade 105 is insulated and the bottom blade 106B (with tapered edge 107B) is conductive (as indicated by the shading). The bottom blade 106B includes a rounded corner 112 for performing continuous cuts when power is activated. The top blade 105 includes a cavity 110 for receiving the aligning member 111 of the bottom blade 106B. The top blade may have a flat edge (107A) or a tapered edge (107B) (as shown). FIGS. 4C and 4D illustrate bipolar embodiments where both blades are conductive. FIG. 4C illustrates the case where the bottom blade 106A has a substantially flat contact surface 107A, while FIG. 4D illustrates the case where the bottom blade 106B has a tapered contact surface 107B.

As with other embodiments described above, the electrosurgical scissors 115 of FIG. 4C may include a scissor body (e.g. a laparoscopic body 100) that includes a switch or lever (e.g. handle 101) that selectively transfers a monopolar output signal from an energy source to the tapered edge 113 of the electrically conductive top scissor blade 105 to electrically cut interlaying tissue located between the electrically conductive top scissor blade 105 and the electrically conductive bottom scissor blade 106.

A vessel sealing instrument may be configured to cauterize and trim tissue. The vessel sealer may include a monopolar scissor type blade cutter such as the electrosurgical scissors shown in FIG. 4A. The vessel sealing instrument may also include a monopolar signal with electrical return through other contact portions of the sealer, such as the scissors shown in FIG. 4B. As explained above, a minimal clearance is provided between blades so that the scissor blades do not touch when closed. The vessel sealing instrument may further include a bipolar scissor type blade cutter (with the energy concentrating features outlined above), such as the scissors shown in FIG. 4C. Again here, a minimal clearance is provided between scissor blades so the blades do not touch when closed.

Other embodiments for a vessel sealer include using the dropdown curved edge 112 as a sliding cutter. The top blade is activated with electrical energy (monopolar) and pushed or pulled through the vessel tissue captured in a closed sealer clamp before or after sealing is completed. In another embodiment, a vessel sealer may be monopolar and may include a return through other contact portions of the sealer (e.g. via aligning member 111), and may be pushed or pulled through the vessel tissue captured in a closed sealer clamp before or after sealing is completed. Still further, a bipolar vessel sealer may include a sliding cutter (with energy concentrating features) that is activated to perform sliding cuts through vessel tissue captured in a closed sealer clamp before or after sealing is completed. The bipolar vessel sealer may include contact portions for transferring electricity, or may include two isolated areas on the scissor blade itself.

In a yet another embodiment, a bipolar electrosurgical scissor instrument is provided. The scissors include a top scissor blade 105 having an electrically conductive tapered edge 113. The tapered edge is insufficiently sharp to shear or otherwise mechanically cut tissue. The electrosurgical scissors also include a bottom electrically conductive scissor blade 106 being movably mounted to the first electrically conductive scissor blade. The second scissor blade 106A has a substantially flat contact surface 107A that is aligned with the tapered edge 113 of the first scissor blade. The electrically conductive bottom blade 106A may be toothed to clamp tissue between the top scissor blade 105 and the bottom scissor blade 106B. The bottom blade may have a flat contact surface (107A) (as shown in FIG. 4C) or a tapered contact surface (107B) (as shown in FIG. 4D).

In a bipolar implementation, the electrical energy may include a substantially continuous waveform supplying substantially continuous electrical energy to the first and second scissor blades (as opposed to the variable pulses of the monopolar implementation). As with the monopolar implementation, the bipolar electrosurgical scissors allow a surgeon or other user to close the scissors to clamp the interlaying tissue. The surgeon can then see what tissue is about to be cut. If he or she does not desire to cut, no electrical energy is applied to the blade(s), and the tissue is not cut. If, however, the user does desire to cut, the user pulls a lever or switch to activate the electrical energy. The scissors then electrically cut the tissue, without shearing it. Because the blades are not sharp enough to shear tissue, the user cannot accidentally nick surrounding tissue or other objects.

In the bipolar implementation, as with the monopolar implementation, the electrosurgical scissors include a scissor body that has a switch or lever (e.g. handle 101) that selectively activates an electrical energy source so that electrical signal is conducted to the tapered edge 113 of the electrically conductive top scissor blade in a first polarity. Conversely, the switch may be located separate from the scissor such as a footswitch activation mechanism. The electrical energy is also transferred to the substantially flat contact surface 107A of the bottom scissor blade in a second, different polarity that is opposite from the first polarity. The transferred energy electrically cuts interlaying tissue located between the electrically conductive top scissor blade and the electrically conductive bottom scissor blade (106A). In this manner, the surgeon can grasp the tissue, determine what is being cut, and then make the cut. Various different blades may be used, along with different active blade scenarios (top blade active, bottom blade active, both blades active, different sections or traces on one blade active, different sections or traces on both blades active, etc.). The blades may also include dropdown curved edges 112 to allow continuous or sliding cuts. The blunt outer edges 108 also allow the scissors to be used for blunt dissections.

Accordingly, monopolar and bipolar electrosurgical scissor embodiments are described. These electrosurgical scissors may be used to electrically cut tissue in a variety of different situations, including in laparoscopic and other minimally invasive surgeries.

Electrosurgical scissor instruments of the present invention may also take the form of scissor-type biopsy cutters. Like the embodiments discussed in connection with FIGS. 1-5, the biopsy cutters of the present invention may be monopolar or bipolar electrosurgical instruments. The biopsy cutters of the present invention may be used to collect tissue samples for analysis. Incorporation of the principles of the present invention into the biopsy cutters enables the biopsy cutters to cut tissue faster, cleaner, and with less thermal damage to the collected tissue sample.

Figure 6:
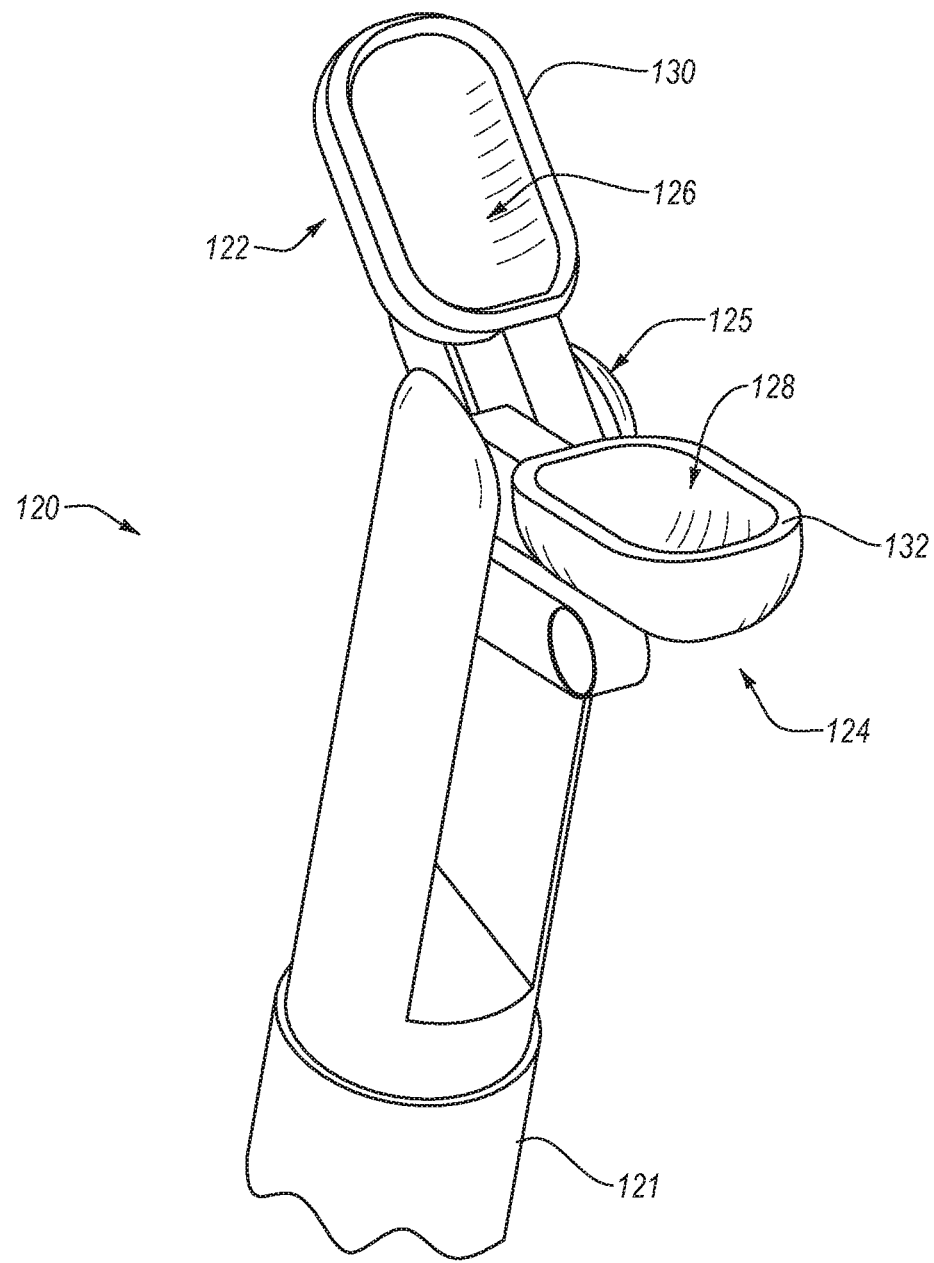
FIG. 6 illustrates an isometric view of a biopsy cutter device according to one embodiment.

FIG. 6 illustrates an exemplary embodiment of a scissor-type biopsy cutter 120 that incorporates the principles of the present invention. Biopsy cutter 120 may be connected to the distal end of an elongated shaft 121. Although not illustrated in FIG. 6, a handle similar to handle 101 may be disposed at the proximal end of elongated shaft 121 to facilitate activation of biopsy cutter 120.

Biopsy cutter 120 has a generally clamshell-like configuration. More specifically, biopsy cutter 120 includes a first half 122 and a second half 124 connected at a hinge 125. As first half 122 and/or second half 124 move about hinge 125, biopsy cutter 120 opens and closes. In other words, as first half 122 and/or second half 124 move about hinge 125, first half 122 and second half 124 are moved closer together or further apart in a scissor-like action. Thus, biopsy cutter 120 may be considered a scissor-type device. Similarly, first half 122 and second half 124 may be considered scissor blades.

As can be seen in FIG. 6, first half 122 includes a cup portion 126 and second half 124 includes a cup portion 128. Cup portions 126, 128 cooperate to form an interior space within biopsy cutter 120 when first half 122 and second half 124 are closed. When a tissue sample is to be retrieved, biopsy cutter 120 may be opened as shown in FIG. 6 and positioned so the desired tissue is between first half 122 and second half 124. Biopsy cutter 120 may then be closed so that the desired tissue is positioned within the interior space formed by cup portions 126, 128.

Similar to the scissor instruments described above, electrical current may flow from first half 122 and/or second half 124 in order to cut out the desired tissue sample. As can be seen in FIG. 6, first half 122 includes a tapered edge 130 that extends around at least a portion of cup portion 126. Second half 124 includes a substantially flat contact surface 132 that extends around at least a portion of cup portion 128 and that is aligned with tapered edge 130. Like tapered edge 113 described above, tapered edge 130 may have a width of about 0.2 mm or less, which allows for a sharpened edge that is not sharp enough to mechanically cut by itself, but which focuses and concentrates the electrical energy in a way that easily cuts through tissue.

In a monopolar situation, first half 122 may be conductive such that electrical current can flow through it and second half 124 may be electrically insulated. In a bipolar situation, both first half 122 and second half 124 may be conductive.

In alternative embodiments, rather than having a substantially flat contact surface 132, second half 124 may include a tapered edge similar to tapered edge 130. In such an embodiment, the instrument may be configured as a monopolar instrument or a bipolar instrument. For instance, in a monopolar situation, either one of first half 122 and second half 124 may be conductive while the other is electrically insulated. In a bipolar situation, first half 122 and second half 124 are both conductive.

Also like the scissors described above in connection with FIGS. 10-5, biopsy cutter 120 may include a coating such as PTFE or other types of fluoropolymers, silicone, other high temperature organic polymers, glass, ceramic, organosilicones and other high temperature combination polymers, diamond, as well as any other high temperature resistant, electrically insulative materials may be used to coat or cover all or portions of first half 122 and/or second half 124. The edge of tapered surface 130 may be fully coated, left uncoated, or cleaned of coating, depending on the insulation value and other coating characteristics of the chosen material in order to focus the electrical energy. In this way, mechanical shearing is eliminated as the cutting mechanism, and tissue may be grasped prior to cutting for evaluation and exclusion of tissues or structures that need to be protected.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An electrosurgical scissor instrument, comprising:
a first electrically conductive scissor blade having opposing generally planar surfaces that are angled relative to one another such that the opposing generally planar surfaces converge to form a tapered edge where the opposing generally planar surfaces meet, the tapered edge being configured to concentrate electrical energy for transmission between the first electrically conductive scissor blade and patient tissue during an electrosurgical procedure, the tapered edge being insufficiently sharp to shear or mechanically cut tissue;
a second scissor blade movably mounted to the first electrically conductive scissor blade, the second scissor blade comprising a contact surface, the contact surface comprising a tapered edge formed by opposing generally planar surfaces that are angled relative to one another such that the opposing generally planar surfaces converge to form the tapered edge where the opposing surfaces meet, the tapered edge being insufficiently sharp to shear or mechanically cut tissue, the tapered edge of the second scissor blade being aligned with the tapered edge of the first electrically conductive scissor blade; and
a scissor body comprising a conductor that transfers electrical energy from an energy source to the tapered edge of the first scissor blade to electrically cut interlaying tissue located between the first scissor blade and the second scissor blade.

2. The electrosurgical scissor instrument of claim 1, wherein the tapered edge of the first scissor blade includes a dropdown rounded corner that allows continuous electrosurgical tissue cutting.

3. The electrosurgical scissor instrument of claim 1, wherein the second scissor blade is electrically conductive.

4. The electrosurgical scissor instrument of claim 1, wherein the second scissor blade is electrically insulated.

5. The electrosurgical scissor instrument of claim 2, wherein the tapered edge of the second scissor blade is electrically insulated.

6. The electrosurgical scissor instrument of claim 1, wherein the tapered edge of the second scissor blade is electrically conductive.

7. The electrosurgical scissor instrument of claim 1, wherein at least a portion of the contact surface of the second scissor blade comprises a substantially flat and electrically insulated edge.

8. The electrosurgical scissor instrument of claim 1, wherein at least a portion of the contact surface of the second scissor blade comprises a substantially flat and electrically conductive edge.

9. The electrosurgical scissor instrument of claim 1, wherein the tapered edge of the first scissor blade has a width of about 0.2 mm or less.

10. The electrosurgical scissor instrument of claim 1, wherein the tapered edge of the second scissor blade has a width of about 0.2 mm or less.

11. A electrosurgical scissor instrument, comprising:
a first electrically conductive scissor blade having opposing generally planar surfaces that are angled relative to one another such that the opposing generally planar surfaces converge to form a tapered edge where the opposing generally planar surfaces meet, the tapered edge being configured to concentrate electrical energy transmission between the first electrically conductive scissor blade and patient tissue during an electrosurgical procedure, the tapered edge being insufficiently sharp to shear or mechanically cut tissue;
a second electrically conductive scissor blade movably mounted to the first electrically conductive scissor blade, the second electrically conductive scissor blade comprising a contact surface, the contact surface comprising a tapered edge formed by opposing generally planar surfaces that are angled relative to one another such that the opposing generally planar surfaces converge to form the tapered edge where the opposing surfaces meet, the tapered edge being configured to concentrate electrical energy for transmission between the second electrically conductive scissor blade and patient tissue during an electrosurgical procedure, the tapered edge of the second electrically conductive scissor blade being aligned with the tapered edge of the first electrically conductive scissor blade, wherein the first electrically conductive scissor blade and the second electrically conductive scissor blade are electrically insulated from one another and wherein a minimum clearance space exists between the first and second electrically conductive scissor blades to prevent the first and second electrically conductive blades from touching; and
a scissor body comprising a conductor that transfers electrical energy from an energy source to at least one of the tapered edge of the first electrically conductive scissor blade and the tapered edge of the second electrically conductive scissor blade to electrically cut interlaying tissue located between the first electrically conductive scissor blade and the second electrically conductive scissor blade.

12. The electrosurgical scissor of claim 11, wherein the tapered edge of the first scissor blade comprises a dropdown rounded corner and the contact surface of the second scissor blade comprises a cavity configured to receive therein at least a portion of the dropdown rounded corner.

13. The electrosurgical scissor of claim 11, wherein at least a portion of the contact surface of the second electrically conductive scissor blade comprises a substantially flat edge.

14. The electrosurgical scissor of claim 11, wherein at least one of the tapered edge of the first electrically conductive scissor blade and the tapered of the second electrically conductive scissor blade has a width of about 0.2 mm or less.

15. A electrosurgical scissor instrument, comprising:
a first electrically conductive scissor blade having a tapered edge that concentrates electrical energy transmitted between the electrosurgical scissor instrument and patient tissue during an electrosurgical procedure, the tapered edge being insufficiently sharp to shear or mechanically cut tissue, the tapered edge of the first scissor blade comprises an interlocking portion;
a second electrically conductive scissor blade movably mounted to the first scissor blade, the second scissor blade comprising a contact surface, the contact surface comprising a tapered edge that concentrates electrical energy transmitted between the electrosurgical scissor instrument and patient tissue during an electrosurgical procedure and that is aligned with the tapered edge of the first scissor blade, the contact surface of the second scissor blade comprises a cavity configured to receive therein at least a portion of the interlocking portion, wherein the first scissor blade and the second scissor blade are electrically insulated from one another and wherein a minimum clearance space exists between the first and second blades to prevent the first and second blades from touching; and a scissor body comprising a conductor that transfers electrical energy from an energy source to at least one of the tapered edge of the first electrically conductive scissor blade and the tapered edge of the second electrically conductive scissor blade to electrically cut interlaying tissue located between the first electrically conductive scissor blade and the second electrically conductive scissor blade.

16. The electrosurgical scissor of claim 15, wherein at least a portion of the contact surface of the second electrically conductive scissor blade comprises a substantially flat edge.

17. The electrosurgical scissor of claim 15, wherein at least one of the tapered edge of the first electrically conductive scissor blade and the tapered of the second electrically conductive scissor blade has a width of about 0.2 mm or less.

\* \* \* \* \*